United States Patent
Cheng et al.

(10) Patent No.: US 9,737,730 B2
(45) Date of Patent: Aug. 22, 2017

(54) PROGRAMMABLE SEGMENTED VOLUMETRIC MODULATED ARC THERAPY FOR RESPIRATORY COORDINATION

(71) Applicant: Jason Chia-Hsien Cheng, Taipei (TW)

(72) Inventors: Jason Chia-Hsien Cheng, Taipei (TW); Jian-Kuen Wu, Taipei (TW)

(73) Assignee: Jason Chia-Hsien Cheng, Taipei (TW)

( * ) Notice: Subject to any disclaimer, the term of this patent is extended or adjusted under 35 U.S.C. 154(b) by 345 days.

(21) Appl. No.: 14/459,705

(22) Filed: Aug. 14, 2014

(65) Prior Publication Data
US 2014/0357931 A1    Dec. 4, 2014

Related U.S. Application Data

(63) Continuation-in-part of application No. 13/364,014, filed on Feb. 1, 2012, now Pat. No. 8,858,414.

(51) Int. Cl.
*A61N 5/10* (2006.01)

(52) U.S. Cl.
CPC .......... *A61N 5/1037* (2013.01); *A61N 5/1047* (2013.01)

(58) Field of Classification Search
CPC .............................. A61N 5/1037; A61N 5/1047
USPC ................................ 600/1; 378/65; 250/492.1
See application file for complete search history.

(56) References Cited

U.S. PATENT DOCUMENTS

2010/0322381 A1   12/2010   Stahl et al.
2010/0329422 A1   12/2010   Brown et al.

OTHER PUBLICATIONS

McGarth et al., Volumetric modulated arc therapy for delivery of hypofractionated stereotactic lung radiotherapy: A dosimetric and treatment efficency analysis, Radiotherapy and Oncology, Jan. 210, pp. 153-157, vol. 95.
Matuszak et al., Clinical Applications of Volumetric Modulated Arc Therapy, Int. J. Radiation Oncology Biol. Phys., Aug. 2009, pp. 608-616, vol. 77, No. 2.
Court et al., Use of realistic breathing lung phantom to evaluate dose delivery errors, Med. Phys., Nov. 2010, pp. 5850-5827 vol. 37.
Qian et al., Dose verification for respiratory-gated volumetric modulated arc therapy, Phys. Med Biol., Jul. 2011, pp. 4827-4838, vol. 56.
Nicolini et al. Pre-clinical evaluation for respiratory-gated delivery of volumetric modulated arc therapy with RapidArc, Phys Med Biol., May 2010, pp. N347-N357, vol. 55.
Chin et al. Investigation of a novel algorithm for true 4D-VMAT planning with comparison to tracked, gated and static delivery, Med Phys., Mar. 2011, pp. 2698-2707, vol. 38, No. 5.

(Continued)

*Primary Examiner* — Christine H Matthews
*Assistant Examiner* — Kaylee Wilson
(74) *Attorney, Agent, or Firm* — WPAT, PC

(57) ABSTRACT

The invention designs a segmented short-arc VMAT plan, modified from the original VMAT plan, to fit the breath-hold interval. The modified VMAT of the invention has the advantages of its applicability to different planning systems for variously long arcs and its preprogrammed arc segmentation for summated dose consistency. The present invention provides a method and a system for use in administering radiation therapy to patients using a radiotherapeutic apparatus with gantry rotation, and also meets the requirements for dose planning and accurate delivery, as well as coordinates patient's breath-hold level.

19 Claims, 5 Drawing Sheets

(56) References Cited

OTHER PUBLICATIONS

Dobler et al. Commissioning of volumetric modulated arc therapy (VMAT) in a dual-vendor environment, Radiotherapy and Oncology, Jan. 2011, pp. 86-89, vol. 99.

Kida et al., 4D-CBCT reconstruction using MV portal imaging during volumetric modulated arc therapy, Radiotherapy and Oncology, Aug. 2011, pp. 380-385, vol. 100.

Ruben et al., The effect of intensity-modulated radiotherapy on radiation-induced second malignancies, Int. J. Radiation Oncology Biol. Phys., Aug. 2008, pp. 1530-1536, vol. 70, No. 5.

Hall et al., Intensity-modulated radiation therapy, protons, and the risk of second cancers, Int. J. Radiation Oncology Biol. Phys., Jan. 2006, pp. 1-7, vol. 65, No. 1.

Bertelsen et al., Single Arc Volumetric Modulated Arc Therapy of head and neck cancer, Radiotherapy and Oncology, Jan. 17, 2010, pp. 142-148, vol. 95.

PROGRAMMABLE SEGMENTED VOLUMETRIC MODULATED ARC THERAPY FOR RESPIRATORY COORDINATION

CROSS REFERENCE TO RELATED APPLICATIONS

This application is a Continuation-in-Part of pending U.S. patent application Ser. No. 13/364,014, "PROGRAMMABLE SEGMENTED VOLUMETRIC MODULATED ARC THERAPY FOR RESPIRATORY COORDINATION", filed on Feb. 1, 2012, which is hereby incorporated by reference in its entirety.

FIELD OF THE INVENTION

The invention relates to a system and a method for volumetric modulated arc therapy (VMAT). In particular, the invention provides a system and a method for programmable segmented VMAT.

BACKGROUND OF THE INVENTION

The recently developed and clinically adopted technique known as volumetric modulated arc therapy (VMAT) improves target conformity and organ sparing by use of rotational intensity modulated radiation therapy (IMRT) and more control points (gantry locations) for intensity optimization (McGrath S D, Matuszak M M, Yan D, Kestin L L, Martinez A A, Grills I. *Volumetric modulated arc therapy for delivery of hypofractionated stereotactic lung radiotherapy: A dosimetric and treatment efficiency analysis. Radiother Oncol* 2010; 95:153-7; Matuszak M M, Yan D, Grills I, Martinez A. *Clinical applications of volumetric modulated arc therapy. Int J Radiat Oncol Biol Phys* 2010; 77:608-16). VMAT is a new type of intensity-modulated radiation therapy (IMRT) treatment technique that uses the same hardware (i.e. a digital linear accelerator) as used for IMRT or conformal treatment, but delivers the radiotherapy treatment using rotational or arc geometry rather than several static beams. This technique uses continuous modulation (i.e. moving the collimator leaves) of the multileaf collimator (MLC) fields, continuous change of the fluence rate (the intensity of the X rays) and gantry rotation speed across a single or multiple 360 degree rotation(s). This significantly reduces beam delivery time compared to conventional fixed field IMRT (otherwise known as step and shoot IMRT). During a VMAT treatment, the Linear Accelerator rotates around the patient while the radiation beam is shaped and reshaped as it is continuously delivered from virtually every angle in a revolution. During a VMAT treatment, specialized software algorithms will vary the three parameters simultaneously: the speed of rotation around the patient, the shape of the MLC aperture, and the dose delivery rate. The target volume dose does not change when using VMAT when the amount of scatter and leakage radiation dose to the rest of the body is reduced compared to conventional IMRT. Varian (Varian Medical Systems, Palo Alto, Calif., USA) develops a VMAT product marketed as RapidArc. The US FDA approved RapidArc for clinical use in February 2008. In its first released software version, only one or two full rotation arcs could be planned. In the second software upgrade (Aria version 8.6) released in the first half of 2009, partial arcs, arcs with exclusion zones (e.g. so that the entry angle through a metallic hip replacement can be avoided) and arcs from different gantry angles (e.g. vertex fields for cranial treatments) allowed greater freedoms of dose intensity modulation for complex target volumes where adjacent critical normal tissue structures need to be avoided.

Elekta (Elekta A B, Stockholm, Sweden) also has a product named VMAT, which does not use Otto's algorithm, but uses a proprietary algorithm. This emphasized multiple arcs from the earliest software releases, in contrast to the early Varian releases. The planning technique for VMAT has evolved with software upgrades. When first introduced, a plan using a double arc to treat a 2 Gray planning target volume (PTV), the first arc optimization is dosed to 1 Gray. The second arc is then optimized to the existing single arc plan, with the smoothing and filling of cold spots and the cooling of hot spots, leading to a more homogenous PTV dosing. With the latest software versions, the planner defines two arcs with starting and stopping positions, and then the optimization occurs to the full 2Gy to the PTV.

U.S. Pat. No. 8,027,431 provides a system and method to receive a radiation treatment plan for delivering at least a portion of a prescribed radiation dose to a target volume in a series of individual treatment beams in an arc around the target volume, each individual treatment beam having a start angle and a stop angle; and deliver a portion of the prescribed radiation dose to the target volume over each of the segmentations, the segmentations arranged in a contiguous manner on the arc and the delivery of the prescribed radiation dose is continuous through the segmentations. However, there has not been a solution to breath-hold coordination for the dynamic delivery of the VMAT system (for example, Eleka VMAT, Elekta Oncology System Ltd., Crawley, West Sussex, UK)

The delivery of each arc of VMAT usually takes more than 1 to 2 minutes, longer than a single tolerable breath hold. Breath hold and respiratory gating are two established strategies for reducing respiration-induced organ motion in radiotherapy. Deep-inspiration breath hold is a controlled breathing technique in which the patient performs a supervised breath hold during radiotherapy, with the dual benefits of reduced respiratory motion from the breath hold and increased normal tissue sparing from the increased tissue volume. Respiratory gating depends on a device external to the patient monitoring breathing and allows delivery of radiation only during certain time intervals, synchronous with the patient's respiratory cycle. Gated radiotherapy requires less patient effort than breath hold, but has more organ motion than static breath hold. Respiration-induced dose-delivery errors are demonstrated with a realistic breathing lung phantom, with exceptionally significant errors by single-arc VMAT using a high dose rate (Court L E, Seco J, Lu X Q, Ebe K, Mayo C, Ionascu D et al. *Use of a realistic breathing lung phantom to evaluate dose delivery errors. Med Phys* 2010; 37:5850-7). Efforts have been made to develop gating solutions to VMAT delivery. Varian's TrueBeam™ (Varian Medical Systems, Palo Alto, Calif., USA) first supported gated VMAT by responding a gating signal from a real-time position management (RPM™) system. Qian et al. adapted a log-file-based dose reconstruction and verified the fidelity of gated VMAT delivery for three patients with lung or pancreatic tumors with three simulated respiratory periods (Qian J, Xing L, Liu W, Luxton G. *Dose verification for respiratory-gated volumetric modulated arc therapy. Phys Med Biol* 2011; 56:4827-38). Preclinical evaluation of Varian's gated RapidArc delivery by use of 2-dimensional dose verification was satisfactorily conducted (Nicolini G, Vanetti E, Clivio A, Fogliata A, Cozzi L. *Pre-clinical evaluation of respiratory-gated delivery of volumetric modulated arc therapy with RapidArc. Phys Med*

*Biol* 2010; 55:N347-57). All the work focuses on Varian's VMAT and RPM™ gating systems, which use the signal of chest wall movement to represent respiratory oscillation and involve complex interactions between MLC kinetics, dose-rate modulation, and gantry rotation. A 4-dimensional VMAT planning framework is under investigation, with the contributions of beams and organ motion from different breathing phases integrated into the optimization process. However, such a strategy is more theoretical than practical for fractionated treatment (Chin E, Otto K. *Investigation of a novel algorithm for true 4D-VMAT planning with comparison to tracked, gated and static delivery. Med Phys* 2011; 38:2698-707). Radiotherapy delivered by Elekta's linear accelerator has used the breath-hold strategy, either by active breathing coordination or passive abdominal compression, to reduce respiration-induced dose errors. Therefore, breath-hold timing and interval are more voluntary and predictable for gated VMAT. To deliver dynamic VMAT within the breath-hold intervals, segmented short arcs of less than 20 to 30 seconds each are required. The available treatment planning systems either have a minimum requirement of gantry rotation range for the arc design, such as 40° arc with the Pinnacle system, or have less satisfactory planning results with short arcs (Bertelsen A, Hansen C R, Johansen J, Brink C. *Single Arc Volumetric Modulated Arc Therapy of head and neck cancer Radiother Oncol* 2010; 95:142-8). To our knowledge, there has not been any gating solution to VMAT delivery by Elekta's accelerator (Dobler B, Groeger C, Treutwein M et al. *Commissioning of volumetric modulated arc therapy (VMAT) in a dual-vendor environment. Radiother Oncol* 2011; 99:86-9; Kida S, Saotome N, Masutani Y et al. 4D-CBCT reconstruction using MV portal imaging during volumetric modulated arc therapy. *Radiother Oncol* 2011; 100:380-5).

The breath-hold method is typically difficult for lung cancer patients, for which a series of segmented shorter arc therapy in VMAT treatment may be necessary, as they cannot hold their breath for extended periods due to compromised pulmonary function. Therefore, there is still a need to provide a solution to breath-hold coordination for patients who receive a VMAT radiotherapy treatment and to meet the requirement for accurate dose delivery at the same time.

SUMMARY OF THE INVENTION

In view of the above, it would be advantageous to have a system and a method to provide programmable and flexible arc therapy in VMAT treatment to fit the breath-hold interval of patients, and this is an objection of the present invention.

The present invention provides a method for use in administering radiation therapy to patients using a radiotherapeutic apparatus with gantry rotation, e.g. Elekta Synergy® linear accelerator, the method comprising:
obtaining an arc with configurable selections of control points and associated MUs (Monitor Unit) defined by a treatment plan; segmenting the arc into a plurality of subarcs according to individual need of a patient; setting a plurality of control points and their associated MUs within each of the subarcs to form a continuous sequence of segmentations arranged on each of the subarcs, wherein each of the subarcs starts on a control point or between two consecutive control points and ends on a control point or between two consecutive control points, with each of the segmentations defining a range over which a prescribed dose of radiation is delivered, and the delivery of the prescribed radiation dose being in a continuous manner throughout the segmentation on each of the subarcs; determining a plurality of weighted doses of radiation and delivered MUs in each of the segmentations, wherein the delivered MUs of each of control point is distributed to be delivered in two adjacent segmentations according to a proportional distribution rule; and turning off the radiation beam when each of the subarcs ends and turning on the radiation beam again when its succeeding subarc starts if a succeeding subarc exists until the treatment is completed.

The present invention also provides a system for use in administering radiation therapy to patients using a radiotherapeutic apparatus with gantry rotation, e.g. Elekta Synergy® linear accelerator, the system can be implemented using an existing treatment planning system in conjunction with a computer system, the system comprising:
a unit for obtaining an arc with configurable selections of control points and associated MUs (Monitor Unit) defined by a treatment plan; a unit for segmenting the arc into a plurality of subarcs according to individual need of a patient; a unit for setting a plurality of control points and their associated MUs (Monitor Unit) within each of the subarcs to form a continuous sequence of segmentations arranged on each of the subarcs, wherein each of the subarcs starts on a control point or between two consecutive control points and ends on a control point or between two consecutive control points, with each of the segmentations defining a range over which a prescribed dose of radiation is delivered, and the delivery of the prescribed radiation dose being in a continuous manner throughout the segmentation on each of the subarcs; a unit for determining a plurality of weighted doses of radiation and delivered MUs in each of the segmentations, wherein the delivered MUs of each of control point is distributed to be delivered in two adjacent segmentations according to a proportional distribution rule; and a unit for controlling the radiation beam to be turned off when each of the subarcs ends and turned on again when its succeeding subarc starts if a succeeding subarc exists until the treatment is completed.

DETAILED DESCRIPTION OF THE INVENTION

Figure 1:
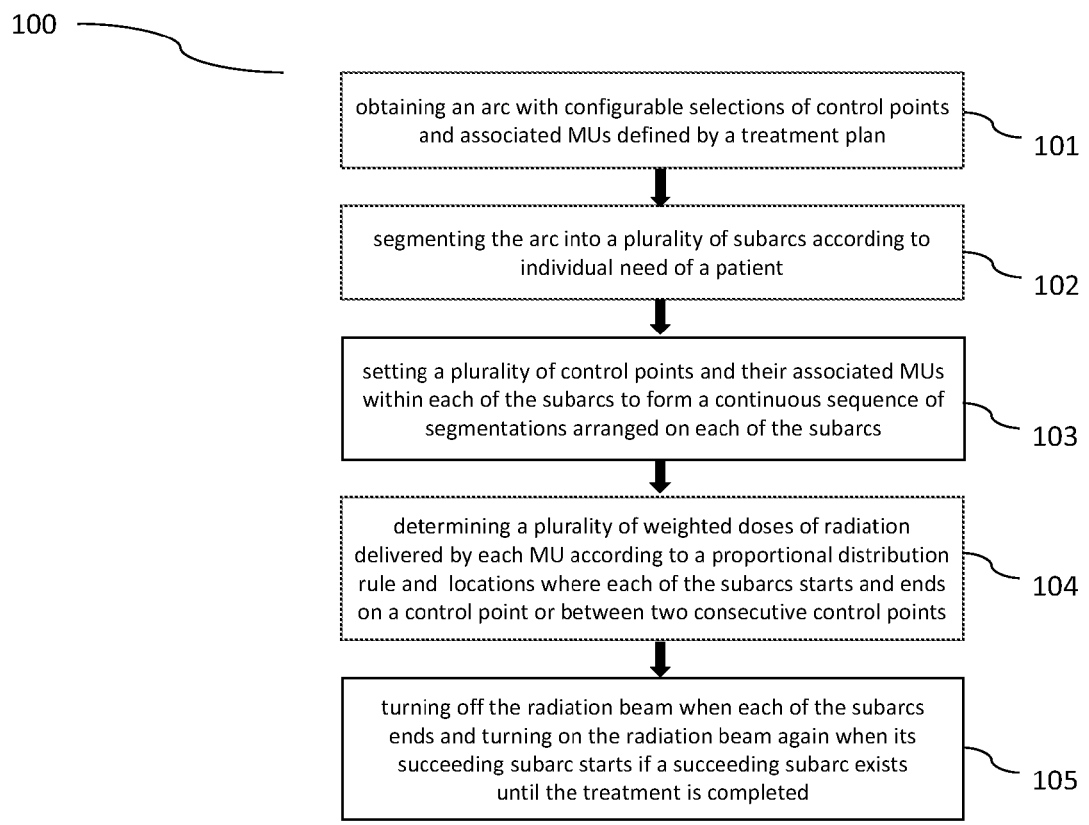
FIG. 1 shows a flowchart depicting a method for use in administering radiation therapy to patients according to an embodiment of the present invention.

The following description is provided to enable any person in the art to make and use the embodiments described herein and sets forth the best mode contemplated therefor. Various modifications, however, will remain readily apparent to those in the art. In describing preferred embodiments of the present invention illustrated in the drawings, specific terminology is employed for the sake of clarity. However, the invention is not intended to be limited to the specific terminology so selected.

The invention designs the programmable segmented short-arc VMAT plan, modified from the original long-arc VMAT, to fit the breath-hold interval of patients and free from the constraints, which the segmented short-arc is not required to start and end on a control point. The modified VMAT of the invention has the advantages of its applicability to different planning systems for variously long arcs and its preprogrammed arc segmentation for summated dose consistency. Using segmented short-arc modification from the original long-arc VMAT plan is accurate for dose planning and delivery, as well as for coordinate patient's breath-hold level. VMAT requires the gantry to accelerate and decelerate frequently to deliver a given angular dose rate (MUdegree).

According to the invention, the monitor units (MUs) of arcs are reassigned between the short arcs. The beam of radiotherapy is delivered by a certain number of machine monitor units (MUs), a measure of machine radiation output. MUs are important as second cancer risk in patients treated with radiotherapy is proportional to how many MUs are needed per treatment course (Hall E J: *Intensity-modulated radiation therapy, protons, and the risk of second cancers, Int J Radiat Oncol Biol Phys* 2006, 65(1):1-7; Ruben J D, Davis S, Evans C, Jones P, Gagliardi F, Haynes M, Hunter A: *The effect of intensity-modulated radiotherapy on radiation-induced second malignancies. Int J Radiat Oncol Biol Phys* 2008, 70(5):1530-6). In the case of a known VMAT arc coming from sequenced static fields, the MUs of the control points between two adjacent segmentations of arc are considered as half-weighted, while the MUs of the control points at the edge are considered for their whole value. According to the invention, the VMAT plans are modified with the revised number of control points, MU weight at each control point, as well as the starting and end gantry angles.

FIG. 1 shows a flowchart depicting a method for use in administering radiation therapy to patients according to an embodiment of the invention. The method 100 includes the following steps: obtaining an arc with configurable selections of control points and associated MUs (Monitor Unit) defined by a treatment plan 101; segmenting the arc into a plurality of subarcs according to individual need of a patient 102; setting a plurality of control points and their associated MUs within each of the subarcs to form a continuous sequence of segmentations arranged on each of the subarcs 103; determining a plurality of weighted doses of radiation and delivered MUs in each of the segmentations according to a proportional distribution rule and locations where each of the subarcs starts and ends on a control point or between two consecutive control points 104; and turning off the radiation beam when each of the subarcs ends and turning on the radiation beam again when its succeeding subarc starts if a succeeding subarc exists until the treatment is completed 105.

In another aspect, the invention provides a system for use in administering radiation therapy to patients using a radiotherapeutic apparatus with gantry rotation, e.g. Elekta Synergy® linear accelerator, the system can be implemented using an existing treatment planning system in conjunction with a computer system, the system comprising: a unit for obtaining an arc with configurable selections of control points and associated MUs (Monitor Unit) defined by a treatment plan; a unit for segmenting the arc into a plurality of subarcs according to individual need of a patient; a unit for setting a plurality of control points and their associated MUs (Monitor Unit) within each of the subarcs to form a continuous sequence of segmentations arranged on each of the subarcs, wherein each of the subarcs starts on a control point or between two consecutive control points and ends on a control point or between two consecutive control points, with each of the segmentations defining a range over which a prescribed dose of radiation is delivered, and the delivery of the prescribed radiation dose being in a continuous manner throughout the segmentation on each of the subarcs; a unit for determining a plurality of weighted doses of radiation and delivered MUs in each of the segmentations, wherein the delivered MUs of each of control point is distributed to be delivered in two adjacent segmentations according to a proportional distribution rule; and a unit for controlling the radiation beam to be turned off when each of the subarcs ends and turned on again when its succeeding subarc starts if a succeeding subarc exists until the treatment is completed.

Figure 2:
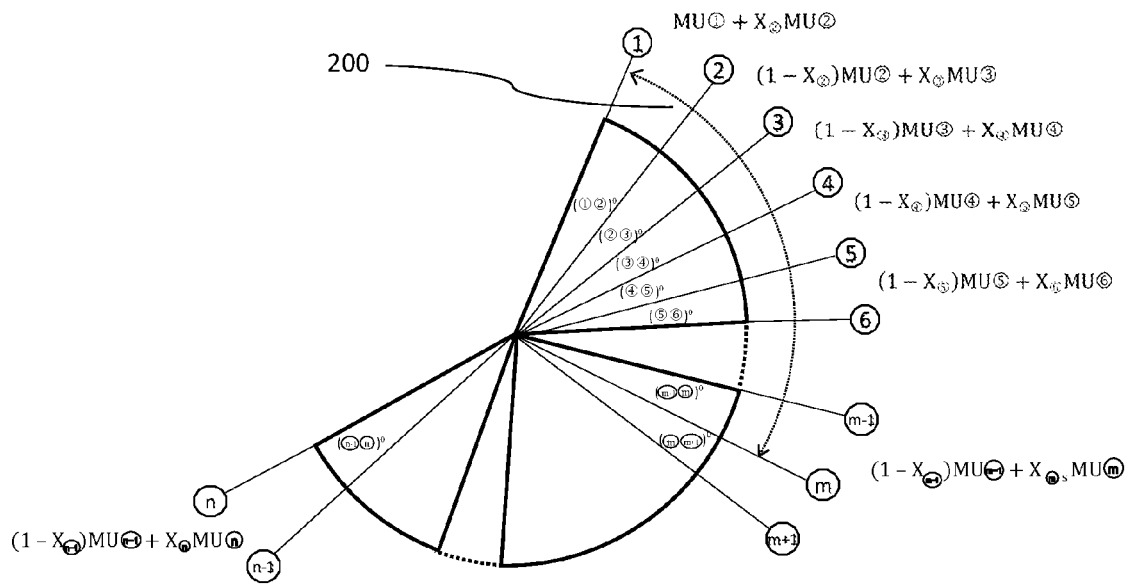
FIG. 2 shows an example for illustrating a dose distribution delivered by each of the segmentations within a subarc according to an embodiment of the present invention.

FIG. 2 shows an example for illustrating a dose distribution delivered by each of the segmentations within a subarc according to an embodiment of the present invention. As shown in FIG. 2, MU① is the monitor units (MUs) designed by the treatment planning system for control point ①; MU② is the MUs designed by the treatment planning system for control point ②; MU③ is the monitor units (MUs) designed by the treatment planning system for control point ③; MU④ is the monitor units (MUs) designed by the treatment planning system for control point ④; MU⑤ is the monitor units (MUs) designed by the treatment planning system for control point ⑤; and MU⑥ is the monitor units (MUs) designed by the treatment planning system for control point ⑥. The rest may be deduced by analogy. The formula between two control points shows the MUs weight for distributing the MUs within each arc between two control points. For example, $X_{②}$ is the proportion of delivered MU of the control point ② distributed for the arc between control points ① and ②, while $(1-X_{②})$ is the proportion of delivered MUs of the control point ② distributed for the arc between control points ② and ③. $X_{③}$ is the proportion of delivered MUs of the control point ③ distributed for the arc between control points ② and ③, while $(1-X_{③})$ is the proportion of delivered MUs of the control point ③ distributed for the arc between control points ③ and ④. The rest may be deduced by analogy. Accordingly, the MUs weight distributed for the arc between control points ② and ③ is represented by $(1-X_{②})$ MU②+$X_{③}$MU③. The angle between control points ①, ② is represented by (①, ②)°. The angle between control points ② and ③ is represented by (②, ③)°. The angle between control points ③ and ④ is represented by (③, ④)°. The rest may be deduced by analogy.

Referring to FIG. 2, the subarc 200 is formed by segmenting a long arc which includes control points ①, ②, ③, ④, . . . ⓝ. The subarc 200 starts and ends on a control point with control point ① as the starting control point and the control point ⓜ as the ending control point. The control point ⓜ is the ending control point of the subarc 200 and is also the starting control point of the succeeding subarc. The subarc 200 can form a continuous sequence of segmentations from $1^{st}$, $2^{nd}$, $3^{rd}$, $4^{th}$, $5^{th}$, . . . $(m-1)^{th}$ segmentation by setting control points ①, ②, ③, ④, . . . and ⓜ and their associated MUs within the subarc 200. Accordingly, the weighted doses of radiation for the first segmentation of the subarc 200 is based on a formula $MU_1+X_2MU_2$ where $X_2$ represents the weighted dose of the delivered $MU_2$, the prescribed dose of radiation to be delivered within the subarc 200 can follow a design by the treatment planning system according to a proportional distribution rule represented by a formula $(1-X_{k-1})\ MU_{k-1}+X_k MU_k$ where $(1-X_{k-1})$ represents a weighted dose of $MU_{k-1}$ and $X_k$ represents a weighted dose of $MU_k$ and when $2 \le k \le (m-1)$ for segmentations denoted as $2^{nd}$, $3^{rd}$, $4^{th}$, $5^{th}$, ... $(m-2)^{th}$ segmentation. Regarding the last segmentation, the weighted dose of radiation is based on a formula $(1-X_{m-1}) MU_{m-1}+X_{ms}MU_m$ where $(1-X_{m-1})$ represents a weighted dose of $MU_{m-1}$ and $X_{ms}$ represents the weighted dose for converting the delivered $MU_m$ between two subarcs. According to one embodiment of the invention, the $MU_1$ of the first (starting) segmentation is 0. According to another embodiment of the invention, $X_{ms}=1$.

Figure 3:
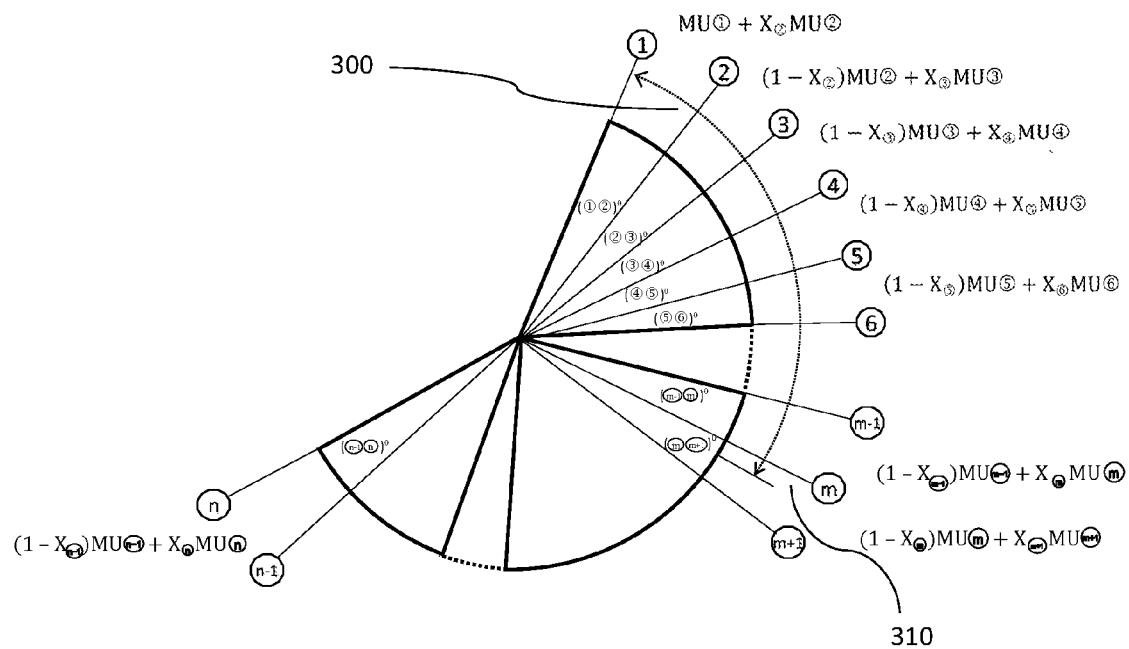
FIG. 3 shows another example for illustrating a dose distribution delivered by each of the segmentations within a subarc according to an embodiment of the present invention.

FIG. 3 shows another example for illustrating a dose distribution delivered by each of the segmentations within a subarc according to an embodiment of the present invention. The subarc 300 is formed by segmenting a long arc which includes control points ①, ②, ③, ④, ... ⓝ. The subarc 300 starts on a control point ① and ends between two control points, i.e. control point ⓜ and control points $(m+1)^{th}$. The subarc 300 can form a continuous sequence of segmentations from $1^{st}$, $2^{nd}$, $3^{rd}$, $4^{th}$, $5^{th}$, ... $m^{th}$ segmentation by setting control points ①, ②, ③, ④, ..., ⓜ, control points $(m+1)^{th}$ and their associated MUs within the subarc 300. Accordingly, the weighted doses of radiation for the first segmentation of the subarc 300 is based on a formula $MU_1+X_2MU_2$ where $X_2$ represents the weighted dose of the delivered $MU_2$, the prescribed dose of radiation in the segmentations denoted as $2^{nd}$, $3^{rd}$, $4^{th}$, $5^{th}$, ... $(m-1)^{th}$ segmentations to be delivered within the subarc 300 can follow a design by the treatment planning system according to a proportional distribution rule represented by a formula $(1-X_{k-1})\ MU_{k-1}+X_k MU_k$ where $(1-X_{k-1})$ represents a weighted dose of $MU_{k-1}$ and $X_k$ represents a weighted dose of $MU_k$ and when $2 \le k \le m$.

Referring to FIG. 3, the MUs weight distributed for the arc between control point ⓜ and control points $(m+1)^{th}$ can be represented by $[(1-X_m)MU_m+X_{m+1}MU_{m+1}]$. According to a proportional distribution rule, a proportional dose distribution for the last segmentation 310, i.e. from control point ⓜ to the end of the subarc 300, is assigned and represented by a formula:

$$[(1-X_m)MU_m+X_{m+1}MU_{m+1}] \times (AR_m+2X_{[m,m+1]s} \times AR_{m+1}) \times AR_m$$

where $(1-X_m)$ represents a weighted dose of $MU_m$, and $X_{m+1}$ represents a weighted dose of $MU_{m+1}$, $X_{[m,m+1]s}$ represents a weighted dose of MU for converting a delivered MUs between two subarcs, $AR_m$ represents an angle between the $m^{th}$ control point and the end of the subarc as a proportion of the angle between the $m^{th}$ control point and the $(m+1)^{th}$ control point, and $AR_{m+1}$ represents an angle between the end of the subarc and the $(m+1)^{th}$ control point as a proportion of the angle between the $m^{th}$ control point and the $(m+1)^{th}$ control point. According to one embodiment of the invention, the $MU_1$ of the first (starting) segmentation is 0. According to another embodiment of the invention, $X_{[m,m+1]s}=1$.

Figure 4:
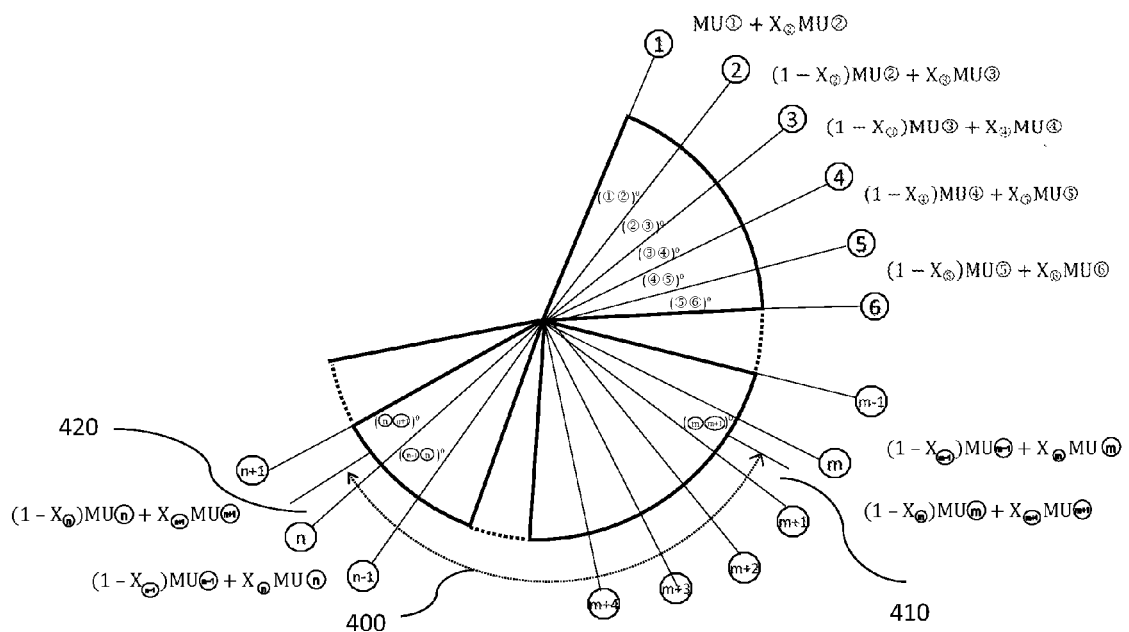
FIG. 4 shows an example for illustrating a dose distribution delivered by each of the segmentations within a succeeding subarc as shown in FIG. 3 according to an embodiment of the present invention.

FIG. 4 shows an example for illustrating a dose distribution delivered by each of the segmentations within a succeeding subarc as shown in FIG. 3 according to an embodiment of the present invention. The subarc 400 can be a succeeding subarc of subarc 300, and the subarc 400 starts between two control points, i.e. control point ⓜ and control points $(m+1)^{th}$, and ends between two control points, i.e. control point ⓝ and control points $(n+1)^{th}$. The subarc 400 can form a continuous sequence of segmentations from $1^{st}$, $2^{nd}$, $3^{rd}$, $4^{th}$, $5^{th}$, ... $(n-m+1)^{th}$ segmentation by setting control points ⓜ, $(m+1)^{th}$, $(m+2)^{th}$, ..., ⓝ, $(n+1)^{th}$ and their associated MUs within the subarc 400. The MUs weight distributed for the arc between control point ⓜ and control points $(m+1)^{th}$ can be represented by $[(1-X_m)MU_m+X_{m+1}MU_{m+1}]$. According to a proportional distribution rule, a proportional dose distribution for the first segmentation 410, i.e. from the start of the subarc 400 to the $(m+1)^{th}$ control point, is assigned and represented by a formula:

$$[(1-X_m)MU_m+X_{m+1}MU_{m+1}] \times [(AR_{m+1}+2(1-X_{[m,m+1]s}) \times AR_m) \times AR_{m+1}]$$

where $(1-X_m)$ represents a weighted dose of $MU_m$, and $X_{m+1}$ represents a weighted dose of $MU_{m+1}$, $X_{[m,m+1]s}$ represents a weighted dose of MU for converting a delivered MUs between two subarc, $AR_m$ represents an angle between the $m^{th}$ control point and the end of the subarc as a proportion of the angle between the $m^{th}$ control point and the $(m+1)^{th}$ control point, and $AR_{m+1}$ represents an angle between the end of the subarc and the $(m+1)^{th}$ control point as a proportion of the angle between the $m^{th}$ control point and the $(m+1)^{th}$ control point. According to another embodiment of the invention, $X_{[m,m+1]s}=1$.

Referring to FIG. 4, the prescribed dose of radiation to be delivered within the middle segmentations of the subarc 400 can follow a design by the treatment planning system according to a proportional distribution rule represented by a formula $(1-X_{k-1})\ MU_{k-1}+X_k MU_k$ where $(1-X_{k-1})$ represents a weighted dose of $MU_{k-1}$ and $X_k$ represents a weighted dose of $MU_k$ and when $m+1 \le k \le n$ for segmentations denoted as $2^{nd}$, $3^{rd}$, $4^{th}$, $5^{th}$, ... $(n-m-1)^{th}$ segmentations. The MUs weight distributed for the arc between control point ⓝ and control points $(n+1)^{th}$ can be represented by $[(1-X_n)MU_n+X_{n+1}MU_{n+1}]$. According to a proportional distribution rule, a proportional dose distribution for the last segmentation 420, i.e. from control point ⓝ to the end of the subarc 400, is assigned and represented by a formula:

$$[(1-X_n)MU_n+X_{n+1}MU_{n+1}] \times (AR_n+2X_{[m,n+1]s} \times AR_{n+1}) \times AR_n$$

where $(1-X_n)$ represents a weighted dose of $MU_n$ and $X_{n+1}$ represents a weighted dose of $MU_{n+1}$, $X_{[n,n+1]s}$ represents a weighted dose of MU for converting a delivered MUs between two subarcs, $AR_n$ represents an angle between the $n^{th}$ control point and the end of the subarc as a proportion of the angle of the $n^{th}$ segmentations, and $AR_{n+1}$ represents an angle between the end of the subarc and the $(n+1)^{th}$ control point as a proportion of the angle of $n^{th}$ segmentations. According to another embodiment of the invention, $X_{[n,n+1]s}=1$.

Figure 5:
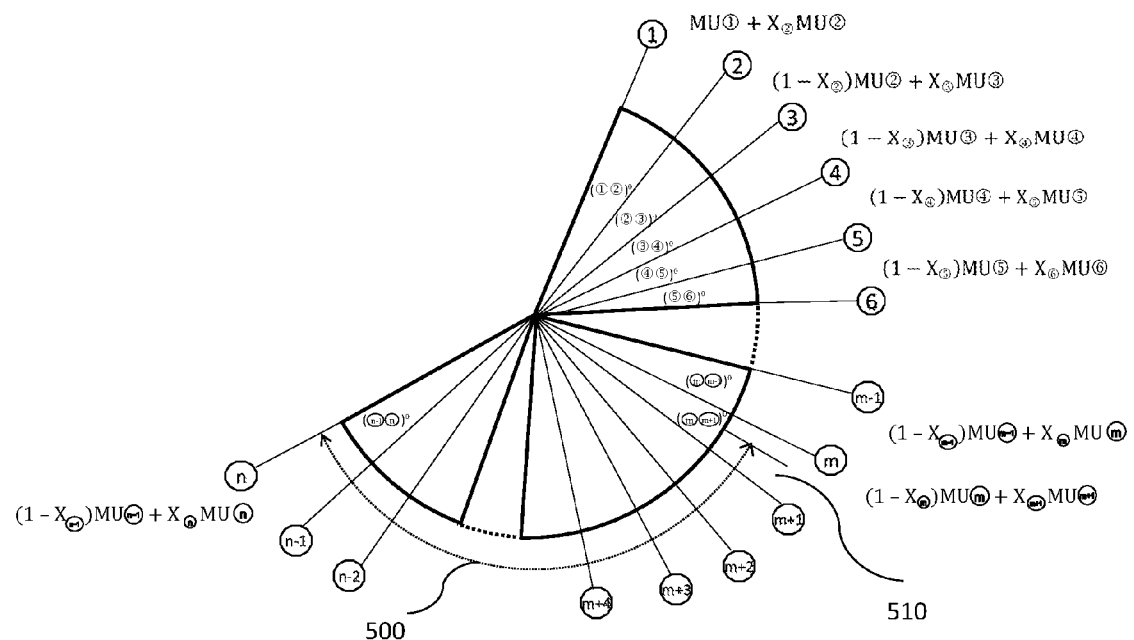
FIG. 5 shows yet another example for illustrating a dose distribution delivered by each of the segmentations within a succeeding subarc as shown in FIG. 3 according to an embodiment of the present invention.

FIG. 5 shows yet another example for illustrating a dose distribution delivered by each of the segmentations within a succeeding subarc as shown in FIG. 3 according to an embodiment of the present invention. The subarc 500 can be a succeeding subarc of subarc 300, and the subarc 500 starts between two control points, i.e. control point ⓒ and control points $(m+1)^{th}$, and ends on a control point ⓝ and control points $(n+1)^{th}$. The subarc 500 can form a continuous sequence of segmentations from $1^{st}$, $2^{nd}$, $3^{rd}$, $4^{th}$, $5^{th}$, ... $(n-m)^{th}$ segmentation by setting control points ⓜ, $(m+1)^{th}$, $(m+2)^{th}$, ⓝ and their associated MUs within the subarc 500. The MUs weight distributed for the arc between control point ⓜ and control points $(m+1)^{th}$ can be represented by $[(1-X_m)MU_m+X_{m+1}MU_{m+1}]$. According to a proportional distribution rule, a proportional dose distribution for the first segmentation 510, i.e. from the start of the subarc 500 to the $(m+1)^{th}$ control point, is assigned and represented by a formula:

$$[(1-X_m)MU_m+X_{m+1}MU_{m+1}]\times[(AR_{m+1}+2(1-X_{[m,m+1]s})\times AR_m)\times AR_{m+1}]$$

where $(1-X_m)$ represents a weighted dose of $MU_m$ and $X_{m+1}$ represents a weighted dose of $MU_{m+1}$, $X_{[m,m+1]s}$ represents a weighted dose of MU for converting a delivered MUs between two subarc, $AR_m$ represents an angle between the $m^{th}$ control point and the end of the subarc as a proportion of the angle between the $m^{th}$ control point and the $(m+1)^{th}$ control point, and $AR_{m+1}$ represents an angle between the end of the subarc and the $(m+1)^{th}$ control point as a proportion of the angle between the $m^{th}$ control point and the $(m+1)^{th}$ control point. According to another embodiment of the invention, $X_{[m,m+1]s}=1$.

Referring to FIG. 5, the prescribed dose of radiation is delivered within the succeeding segmentations of the subarc 500 and the weighted doses of radiation delivered within each of the segmentations is represented by a formula $(1-X_{k-1})MU_{k-1}+X_kMU_k$ where $(1-X_{k-1})$ represents a weighted dose of $MU_{k-1}$ and $X_k$ represents a weighted dose of $MU_k$ and when $m+1 \leq k \leq (n-1)$ for segmentations denoted as $2^{nd}$, $3^{rd}$, $4^{th}$, $5^{th}$, ... $(n-m-2)^{th}$ segmentations, and the weighted dose of radiation for the last segmentation, i.e. the $(n-m-1)^{th}$ segmentation, is based on a formula $(1-X_{n-1})MU_{n-1}+X_{ns}MU_n$ where $(1-X_{n-1})$ represents a weighted dose of $MU_{n-1}$ and $X_{ns}$ represents the weighted dose for converting the delivered $MU_n$ between two subarc. According to another embodiment of the invention, $X_{[n,n+1]s}=1$.

In some embodiments, the radiation treatment plan is provided to the radiation therapy treatment delivery system embodied in a computer or processor readable medium such as a file or series of files embodied in a memory storage unit. The system of the invention may be implemented as an optical disk, a CD-ROM, RAM, a flash ROM, or any type of memory storage unit now known or that becomes known in the future.

The method and system of the invention provide individualized treatment planning modification for VMAT and propose to a solution to divide the long arc from the original VMAT plan into split short arcs, with each short-arc delivery taking less than a single breath hold. The method and system can be incorporated into any of conventional VMAT plans to solve the problem of the conventional VMAT plans in lacking coordination of VMAT and breath-hold interval.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A programmable method for use in administering radiation therapy using a radiotherapeutic apparatus with gantry rotation to reduce a dose delivery time, the method comprising:

obtaining an arc with configurable selections of control points and associated monitor units (MUs) defined by a volumetric modulated arc therapy (VMAT) treatment plan;

segmenting the arc into a plurality of subarcs;

setting a plurality of the control points and associated MUs within each of the subarcs to form a continuous sequence of segmentations arranged on each of the subarcs, wherein each of the subarcs starts on a first control point or between two consecutive control points and ends on a second control point or between two consecutive control points, with each of the segmentations defining a range for delivering a prescribed dose of radiation, and the prescribed radiation dose is delivered in a continuous manner throughout the segmentation on each of the subarcs;

determining a plurality of weighted doses of radiation and delivered MUs in each of the segmentations, wherein the delivered MUs of each of the control points are distributed to be delivered in two adjacent segmentations according to a proportional distribution rule;

turning off the radiation beam when each of the subarcs ends and turning on the radiation beam again when a succeeding subarc starts, if a succeeding subarc exists, until the treatment is completed.

2. The programmable method of claim 1, wherein each of the subarcs requires less delivery time than a single breath-hold.

3. The programmable method of claim 1, wherein if one of the subarc starts on the first control point and ends on the second control point, denoted as $1^{st}$ and $m^{th}$ control points respectively, the prescribed dose of radiation to be delivered within the subarc is based on a proportional distribution rule represented by a formula $(1-X_{k-1})MU_{k-1}+X_kMU_k$ where $(1-X_{k-1})$ represents a weighted dose of $MU_{k-1}$ and $X_k$ represents a weighted dose of $MU_k$ and when $2 \leq k \leq (m-1)$ for segmentations denoted as $2^{nd}$, $3^{rd}$, $4^{th}$, $5^{th}$, ... $(m-2)^{th}$ segmentations, while the weighted doses of radiation for a first segmentation is based on a formula $MU_1+X_2MU_2$ where $X_2$ represents a weighted dose of the delivered $MU_2$ and a weighted dose of radiation for a last segmentation, denoted as $(m-1)^{th}$ segmentation, is based on a formula $(1-X_{m-1})MU_{m-1}+X_{ms}MU_m$ where $(1-X_{m-1})$ represents a weighted dose of $MU_{m-1}$ and $X_{ms}$ represents a weighted dose for converting the delivered $MU_m$ between two subarcs.

4. The programmable method of claim 1, wherein if one of the subarc starts from the first control point, denoted as $1^{st}$ control point, and ends between two control points, denoted as between $m^{th}$ and $(m+1)^{th}$ control points, the prescribed dose of radiation to be delivered within preceding segmentations of the subarc is based on a formula $MU_1+X_2MU_2$ for a first segmentation where $X_2$ represents a weighted dose of the delivered $MU_2$ and the weighted doses of radiation delivered within each of the segmentations are represented by another formula $(1-X_{k-1})MU_{k-1}+X_kMU_k$ where $(1-X_{k-1})$ represents a weighted dose of $MU_{k-1}$ and $X_k$ represents a weighted dose of $MU_k$ and when $2 \leq k \leq m$ for segmentations denoted as $2^{nd}$, $3^{rd}$, $4^{th}$, $5^{th}$, ... $(m-1)^{th}$ segmentations, while a proportional dose distribution for a last segmentation between the $m^{th}$ control point to the end of the subarc is assigned according to a proportional distribution rule, represented by a formula $[(1-X_m)MU_m+X_{m+1}MU_{m+1}]\times(AR_m+2X_{[m,m+1]s}\times AR_{m+1})\times AR_m$ where $(1-X_m)$ represents a weighted dose of $MU_m$, and $X_{m+1}$ represents a weighted dose of $MU_{m+1}$, $X_{[m,m+1]s}$ represents a weighted dose of MU for converting delivered MUs between two subarcs, $AR_m$ represents an angle between the $m^{th}$ control point and the end of the subarc as a proportion of an angle between the $m^{th}$ control point and the $(m+1)^{th}$ control point, and $AR_{m+1}$ represents an angle between the end of the subarc and the $(m+1)^{th}$ control point as a proportion of the angle between the $m^{th}$ control point and the $(m+1)^{th}$ control point.

5. The method of claim 4, wherein the $MU_1$ of the first segmentation is 0 and $X_{[m, m+1]s}$ is 1.

6. The programmable method of claim 1, wherein if one of the subarcs starts between two control points, denoted as $m^{th}$ and $(m+1)^{th}$ control points, and ends on a control point, denoted as $n^{th}$ control point, a proportional dose distribution for a first segmentation between the start of the subarc to the $(m+1)^{th}$ control point is assigned according to a proportional distribution rule, represented by a formula $[(1-X_m)MU_m + X_{m+1}MU_{m+1}] \times [(AR_{m+1}+2(1-X_{[m, m+1]s}) \times AR_m) \times AR_{m+1}]$ where $(1-X_m)$ represents a weighted dose of $MU_m$, $X_{m+1}$ represents a weighted dose of $MU_{m+1}$ $X_{[m, m+1]s}$ represents a weighted dose of MU for converting delivered MUs at the end of non-control point into a starting control point of the succeeding subarc, $X_{[m, m+1]s}$ represents a weighted dose of MU for converting a delivered MUs between two subarcs, $AR_m$ represents an angle between the $m^{th}$ control point and the end of the subarc as a proportion of an angle between the $m^{th}$ control point and the $(m+1)^{th}$ control point, $AR_{m+1}$ represents an angle between the end of the subarc and the $(m+1)^{th}$ control point as a proportion of the angle between the $m^{th}$ control point and the $(m+1)^{th}$ control point, while the prescribed dose of radiation is delivered within the succeeding segmentations of the subarc and a weighted doses of radiation delivered within each of the segmentations is represented by a formula $(1-X_{k-1})MU_{k-1}+X_k MU_k$ where $(1-X_{k-1})$ represents a weighted dose of $MU_{k-1}$ and $X_k$ represents a weighted dose of $MU_k$ and when $m+1 \leq k \leq (n-1)$ for segmentations denoted as $2^{nd}, 3^{rd}, 4^{th}, 5^{th}, \ldots (n-m-2)^{th}$ segmentations, and the weighted dose of radiation for the last segmentation, denoted as $(n-m-1)^{th}$ segmentation, is based on a formula $(1-X_{n-1})MU_{n-1}+X_m MU_n$ where $(1-X_{n-1})$ represents a weighted dose of $MU_{n-1}$ and $X_{ns}$ represents a weighted dose for converting the delivered $MU_n$ between two subarcs.

7. The programmable method of claim 1, wherein if one of the subarcs starts between two control points, denoted as $m^{th}$ and $(m+1)^{th}$ control points, and ends between two control points, denoted as $n^{th}$ and $(n+1)^{th}$ control points, a proportional dose distribution for a first segmentation between the start of the subarc to the $(m+1)^{th}$ control point is assigned according to a proportional distribution rule, represented by a formula $[(1-X_m)MU_m+X_{m+1}MU_{m+1}] \times [(AR_{m+1}+2(1-X_{[m, m+1]s}) \times AR_{m+1}]$ where $(1-X_m)$ represents a weighted dose of $MU_m$, and $X_{m+1}$ represents a weighted dose of $MU_{m+1}$, $X_{[m, m+1]s}$ represents a weighted dose of MU for converting delivered MUs between two subarcs, $AR_m$ represents an angle between the $m^{th}$ control point and the end of the subarc as a proportion of an angle between the $m^{th}$ control point and the $(m+1)^{th}$ control point, $AR_{m+1}$ represents an angle between the end of the sub arc and the $(m+1)^{th}$ control point as a proportion of the angle between the $m^{th}$ control point and the $(m+1)^{th}$ control point;

the prescribed dose of radiation to be delivered within the middle segmentations of the subarc is based on a proportional distribution rule represented by a formula $(1-X_{k-1})MU_{k-1}+X_k MU_k$ where $(1-X_{k-1})$ represents a weighted dose of $MU_{k-1}$ and $X_k$ represents a weighted dose of $MU_k$ and when $m+1 \leq k \leq n$ for segmentations denoted as $2^{nd}, 3^{rd}, 4^{th}, 5^{th}, \ldots (n-m-1)^{th}$ segmentations, while a proportional dose distribution for a last segmentation between the $n^{th}$ control point to the end of the subarc is assigned according to a proportional distribution rule, represented by a formula $[(1-X_n)MU_n+X_{n+1}MU_{n+1}] \times (AR_n+2X_{[n,n+1]s} \times AR_{n+1}) \times AR_n$ where $(1-X_n)$ represents a weighted dose of $MU_n$ and $X_{n-1}$ represents a weighted dose of $MU_{n+1}$, $X_{[n, n-1]s}$ represents a weighted dose of MU for converting delivered MUs between two subarcs, $AR_n$ represents an angle between the $n^{th}$ control point and the end of the subarc as a proportion of an angle between the $n^{th}$ control point and the $(n+1)^{th}$ control point, and $AR_{n+1}$ represents an angle between the end of the sub arch and the $(n+1)^{th}$ control point as a proportion of the angle between the $n^{th}$ control point and the $(n+1)^{th}$ control point.

8. The programmable method of claim 1, wherein the radiotherapeutic apparatus decelerates gantry angular speed and compensates an increasing dose rate due to the radiation beam turned off when each of the subarcs ends.

9. The programmable method of claim 1, wherein the radiotherapeutic apparatus accelerates gantry angular speed and compensates an increasing dose rate due to the radiation beam turned on again when the succeeding subarc starts if a succeeding subarc exists.

10. A system for administering radiation therapy to patients using a radiotherapeutic apparatus with gantry rotation, the system comprising:
a non-transitory memory storage medium configured to execute a treatment plan stored in said non-transitory memory storage medium; and
a processor comprising:
a unit for obtaining an arc with configurable selections of control points and associated MUs (Monitor Unit) defined by the treatment plan, wherein the treatment plan is a VMAT (volumetric modulated arc therapy) treatment plan;
a unit for segmenting the arc into a plurality of subarcs according to individual need of a patient;
a unit for setting a plurality of the control points and associated MUs within each of the subarcs to form a continuous sequence of segmentations arranged on each of the subarcs, wherein each of the subarcs starts on a first control point or between two consecutive control points and ends on a second control point or between two consecutive control points, with each of the segmentations defining a range over which a prescribed dose of radiation is delivered, and the delivery of the prescribed radiation dose being in a continuous manner throughout the segmentation on each of the subarcs;
a unit for determining a plurality of weighted doses of radiation and delivered MUs in each of the segmentations, wherein the delivered MUs of each of the control points are distributed to be delivered in two adjacent segmentations according to a proportional distribution rule; and
a unit for controlling a radiation beam to be turned off when each of the subarcs ends and turned on again when a succeeding subarc starts, if a succeeding subarc exists, until the treatment is completed.

11. The system of claim 10, wherein each of the subarcs requires less delivery time than a single breath-hold.

12. The system of claim 10, wherein if one of the subarc starts on said first control point and ends on the second control point, denoted as $1^{st}$ and $m^{th}$ control points respectively, the prescribed dose of radiation to be delivered within the subarc is based on a proportional distribution rule represented by a formula $(1-X_{k-1}) MU_{k-1}+X_k MU_k$ where $(1-X_{k-1})$ represents a weighted dose of $MU_{k-1}$ and $X_k$ represents a weighted dose of $MU_k$ and when $2 \le k \le (m-1)$ for segmentations denoted as $2^{nd}, 3^{rd}, 4^{th}, 5^{th}, \ldots (m-2)^{th}$ segmentations, while the weighted doses of radiation for a first segmentation is based on a formula $MU_1+X_2MU_2$ where $X_2$ represents a weighted dose of the delivered $MU_2$ and a weighted dose of radiation for a last segmentation, denoted as $(m-1)^{th}$ segmentation, is based on a formula $(1-X_{m-1})MU_{m-1}+X_{ms}MU_m$ where $(1-X_{m-1})$ represents a weighted dose of $MU_{m-1}$ and $X_{ms}$ represents a weighted dose for converting the delivered $MU_m$ at the stopping control point to that at the starting control point of the succeeding subarc.

13. The system of claim 12, wherein the $MU_1$ of the first segmentation is 0 and $X_{[m, m+1]s}$ is 1.

14. The system of claim 10, wherein if one of the subarc starts from the first control point, denoted as $1^{st}$ control point, and ends between two control points, denoted as between $m^{th}$ and $(m+1)^{th}$ control points, the prescribed dose of radiation to be delivered within preceding segmentations of the subarc is based on a formula $MU_1+X_2MU_2$ for a first segmentation where $X_2$ represents a weighted dose of the delivered $MU_2$ and the weighted doses of radiation delivered within each of the segmentations are represented by another formula $(1-X_{k-1}) MU_{k-1}+X_k MU_k$ where $(1-X_{k-1})$ represents a weighted dose of $MU_{k-1}$ and $X_k$ represents a weighted dose of $MU_k$ and when km for segmentations denoted as $2^{nd}, 3^{rd}, 4^{th}, 5^{th}, \ldots (m-1)^{th}$ segmentations, while a proportional dose distribution for a last segmentation between the $m^{th}$ control point to the end of the subarc is assigned according to a proportional distribution rule, represented by a formula $[(1-X_m)MU_m+X_{m+1}MU_{m+1}]\times(AR_m+2X_{[m, m+1]s}\times AR_{m+1})\times AR_m$ where $(1-X_m)$ represents a weighted dose of $MU_m$, and $X_{m+1}$ represents a weighted dose of $MU_{m+1}$, $X_{[m, m+1]s}$ represents a weighted dose of MU for converting a delivered MUs between two subarcs, $AR_m$ represents an angle between the $m^{th}$ control point and the end of the subarc as a proportion of an angle between the $m^{th}$ control point and the $(m+1)^{th}$ control point, and $AR_{m+1}$ represents an angle between the end of the subarc and the $(m+1)^{th}$ control point as a proportion of the angle between the $m^{th}$ control point and the $(m+1)^{th}$ control point.

15. The system of claim 10, wherein if one of the subarcs starts between two control points, denoted as $m^{th}$ and $(m+1)^{th}$ control points, and ends on a control point, denoted as $n^{th}$ control point, a proportional dose distribution for a first segmentation between the start of the subarc to the $(m+1)^{th}$ control point is assigned according to a proportional distribution rule, represented by a formula $[(1-X_m)MU_m+X_{m+1}MU_{m+1}]\times[(AR_{m+1}+2(1-X_{[m, m+1]s})\times AR_m)\times AR_{m+1}]$ where $(1-X_m)$ represents a weighted dose of $MU_m$, $X_{m+1}$ represents a weighted dose of $MU_{m+1}$ $X_{[m, m+1]s}$ represents a weighted dose of MU for converting delivered MUs at the end of non-control point into a starting control point of the succeeding subarc, $X_{[m, m+1]s}$ represents a weighted dose of MU for converting a delivered MUs between two subarcs, $AR_m$ represents an angle between the $m^{th}$ control point and the end of the subarc as a proportion of an angle between the $m^{th}$ control point and the $(m+1)^{th}$ control point, $AR_{m+1}$ represents an angle between the end of the subarc and the $(m+1)^{th}$ control point as a proportion of the angle between the $m^{th}$ control point and the $(m+1)^{th}$ control point, while the prescribed dose of radiation is delivered within the succeeding segmentations of the subarc and a weighted doses of radiation delivered within each of the segmentations is represented by a formula $(1-X_{k-1}) MU_{k-1}+X_k MU_k$ where $(1-X_{k-1})$ represents a weighted dose of $MU_{k-1}$ and $X_k$ represents a weighted dose of $MU_k$ and when $m+1 \le k \le (n-1)$ for segmentations denoted as $2^{nd}, 3^{rd}, 4^{th}, 5^{th}, \ldots (n-m-2)^{th}$ segmentations, and the weighted dose of radiation for the last segmentation, denoted as $(n-m-1)^{th}$ segmentation, is based on a formula $(1-X_{n-1})MU_{n-1}+X_m MU_n$ where $(1-X_{n-1})$ represents a weighted dose of $MU_{n-1}$ and $X_{ns}$ represents a weighted dose for converting the delivered $MU_n$ between two subarcs.

16. The system of claim 10, wherein if one of the subarcs starts between two control points, denoted as $m^{th}$ and $(m+1)^{th}$ control points, and ends between two control points, denoted as $n^{th}$ and $(n+1)^{th}$ control points, a proportional dose distribution for a first segmentation between the start of the subarc to the $(m+1)^{th}$ control point is assigned according to a proportional distribution rule, represented by a formula $[(1-X_m)MU_m+X_{m+1}MU_{m+1}]\times[(AR_{m+1}+2(1-X_{[m, m+1]s})\times AR_{m+1}]$ where $(1-X_m)$ represents a weighted dose of $MU_m$, and $X_{m+1}$ represents a weighted dose of $MU_{m+1}$, $X_{[m, m+1]s}$ represents a weighted dose of MU for converting delivered MUs between two subarcs, $AR_m$ represents an angle between the $m^{th}$ control point and the end of the subarc as a proportion of an angle between the $m^{th}$ control point and the $(m+1)^{th}$ control point, $AR_{m+1}$ represents an angle between the end of the sub arc and the $(m+1)^{th}$ control point as a proportion of the angle between the $m^{th}$ control point and the $(m+1)^{th}$ control point;

the prescribed dose of radiation to be delivered within the middle segmentations of the subarc is based on a proportional distribution rule represented by a formula $(1-X_{k-1}) MU_{k-1}+X_k MU_k$ where $(1-X_{k-1})$ represents a weighted dose of $MU_{k-1}$ and $X_k$ represents a weighted dose of $MU_k$ and when $m+1 \le k \le n$ for segmentations denoted as $2^{nd}, 3^{rd}, 4^{th}, 5^{th}, \ldots (n-m-1)^{th}$ segmentations, while a proportional dose distribution for a last segmentation between the $n^{th}$ control point to the end of the subarc is assigned according to a proportional distribution rule, represented by a formula $[(1-X_n)MU_n+X_{n+1}MU_{n+1}]\times(AR_n+2X_{[n, n+1]s}\times AR_{n+1})\times AR_n$ where $(1-X_n)$ represents a weighted dose of $MU_n$ and $X_{n-1}$ represents a weighted dose of $MU_{n+1}$, $X_{[n,n-1]s}$ represents a weighted dose of MU for converting delivered MUs between two subarcs, $AR_n$ represents an angle between the $n^{th}$ control point and the end of the subarc as a proportion of an angle between the $n^{th}$ control point and the $(n+1)^{th}$ control point, and $AR_{n+1}$ represents an angle between the end of the sub arch and the $(n+1)^{th}$ control point as a proportion of the angle between the $n^{th}$ control point and the $(n+1)^{th}$ control point.

17. The system of claim 10, wherein the radiotherapeutic apparatus decelerates gantry angular speed and compensates an increasing dose rate due to the radiation beam being turned off when each of the subarcs ends.

18. The system of claim 10, wherein the radiotherapeutic apparatus accelerates gantry angular speed and compensates an increasing dose rate due to the radiation beam being turned on again when the succeeding subarc starts if a succeeding subarc exists.

19. A programmable method for setting subarcs in a segmented short-arc volumetric modulated arc therapy (VMAT) to fit a breath-hold interval, comprising the following steps:
(a) dividing an arc in the VMAT into a plurality of subarcs;
(b) setting a plurality of cut-edge control points within each subarc to form a plurality of segments, each segment defining a range over which a prescribed dose of radiation is delivered with the segments arranged in a continuous manner on the subarc and the delivery of the prescribed radiation dose being continuous through the segments;
(c) setting monitor units (MUs) for the segments within each subarc, wherein the monitor units are designated as $MU_n$ and $MU_{n+1}$ respectively, n is an integer; and
(d) determining a dose distribution within each subarc by setting delivered MUs in each segment, wherein the delivered MUs in a $n^{th}$ segment are distributed according to a formula: $MU_n + X_{n+1} MU_{n+1}$; the delivered MUs in a $(n+1)^{th}$ segment are distributed according to a formula: $(1-X_{n+1}) MU_{n+1} + X_{n+2} MU_{n+2}$; $X_{n-1}$ is a proportion of the delivered MUs distributed for the $n^{th}$ segment, while $(1-X_{n+1})$ is a proportion of the delivered MUs distributed for the $(n+1)^{th}$ segment; and $X_{n+1}$ is a proportion for converting the delivered MUs if $X_{n+1}$ is a last control point of a current subarc and a starting control point of a subsequent subarc;
wherein each subarc is in an interval less than a single breath-hold.

* * * * *